United States Patent
Suzuki

(10) Patent No.: US 11,964,239 B2
(45) Date of Patent: Apr. 23, 2024

(54) ZEOLITE MEMBRANE COMPOSITE, AND SEPARATION METHOD AND PRODUCTION METHOD OF BRANCHED DIOLEFIN USING SAME

(71) Applicant: ZEON CORPORATION, Tokyo (JP)

(72) Inventor: Takahiro Suzuki, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 306 days.

(21) Appl. No.: 17/593,158

(22) PCT Filed: Mar. 18, 2020

(86) PCT No.: PCT/JP2020/012057
§ 371 (c)(1),
(2) Date: Sep. 10, 2021

(87) PCT Pub. No.: WO2020/196176
PCT Pub. Date: Oct. 1, 2020

(65) Prior Publication Data
US 2022/0184563 A1 Jun. 16, 2022

(30) Foreign Application Priority Data

Mar. 26, 2019 (JP) .................................. 2019-059017

(51) Int. Cl.
| | | |
|---|---|---|
| *B01D 69/10* | (2006.01) | |
| *B01D 69/12* | (2006.01) | |
| *B01D 71/02* | (2006.01) | |
| *C07C 7/144* | (2006.01) | |

(52) U.S. Cl.
CPC ............. *B01D 69/12* (2013.01); *B01D 69/10* (2013.01); *B01D 71/028* (2013.01); *C07C 7/144* (2013.01); *B01D 2325/02* (2013.01)

(58) Field of Classification Search
CPC ....... C07C 7/144; C07C 11/18; C07C 61/366; C01B 39/26; B01D 53/228; B01D 61/36; B01D 67/0051; B01D 69/10; B01D 69/12; B01D 2325/02; B01D 2256/24; B01D 2257/702; B01J 29/18; B01J 29/22; B01J 29/26; B01J 20/18; B01J 2229/42; B01J 2229/186; B01J 2229/350006; B01J 35/065; B01J 37/0201; B01J 37/0215; B01J 37/370246; B01J 37/30
USPC ........ 502/4, 60, 64, 66, 69, 74, 78; 585/601, 585/818, 820
See application file for complete search history.

(56) References Cited

U.S. PATENT DOCUMENTS

| | | | |
|---|---|---|---|
| 5,831,139 A | 11/1998 | Schmidt et al. | |
| 6,692,640 B2 * | 2/2004 | Matsukata | B01D 71/028 |
| | | | 502/64 |
| 8,679,412 B2 | 3/2014 | Yamashita et al. | |
| 9,527,785 B2 | 12/2016 | Blackmon et al. | |
| 2017/0259214 A1 | 9/2017 | Onozuka et al. | |
| 2017/0349510 A1 | 12/2017 | Matsukata et al. | |

FOREIGN PATENT DOCUMENTS

| | | |
|---|---|---|
| JP | 2002348579 A | 12/2002 |
| JP | 2003144871 A | 5/2003 |
| JP | 2012067091 A | 4/2012 |
| JP | 2015174081 A | 10/2015 |
| WO | 9601687 A1 | 1/1996 |
| WO | 2011118777 A1 | 9/2011 |
| WO | 2016084845 A1 | 6/2016 |
| WO | 2016098417 A1 | 6/2016 |

OTHER PUBLICATIONS

Machine Translation of JP 2003-117871 A, (2003), 1-14.*
Tanaka et al., "Preparation and gas permeance of c-axis oriented zeolite membrane using ion-exchanged mordenite zeolite crystals oriented in magnetic field", Journal of the European Ceramic Society, 40 (2020) 5984-5990.*
Machine Translation of JP-2003144871 A (2003), 1-14.*
Machine Translation of WO 2016/084845 (2016), 1-15.*
Aug. 30, 2022, Office Action issued by the Intellectual Property Office of Singapore in the corresponding Singaporean Patent Application No. 11202108995R.
Jun. 9, 2020, International Search Report issued in the International Patent Application No. PCT/JP2020/012057.
Nov. 29, 2022, the Extended European Search Report issued by the European Patent Office in the corresponding European Patent Application No. 20776438.2.
Sep. 28, 2021, International Preliminary Report on Patentability issued in the International Patent Application No. PCT/JP2020/012057.
Nov. 30, 2023, Office Action issued by the Intellectual Property Office of Vietnam in the corresponding Vietnamese Patent Application No. 1-2021-05082.

* cited by examiner

*Primary Examiner* — Elizabeth D Wood
(74) *Attorney, Agent, or Firm* — KENJA IP LAW PC

(57) ABSTRACT

A zeolite membrane composite includes a porous support and a zeolite membrane formed on at least one surface of the porous support. The zeolite membrane of the zeolite membrane composite is formed of an X-MOR-type zeolite, where X includes at least one type of transition metal ion.

6 Claims, 1 Drawing Sheet

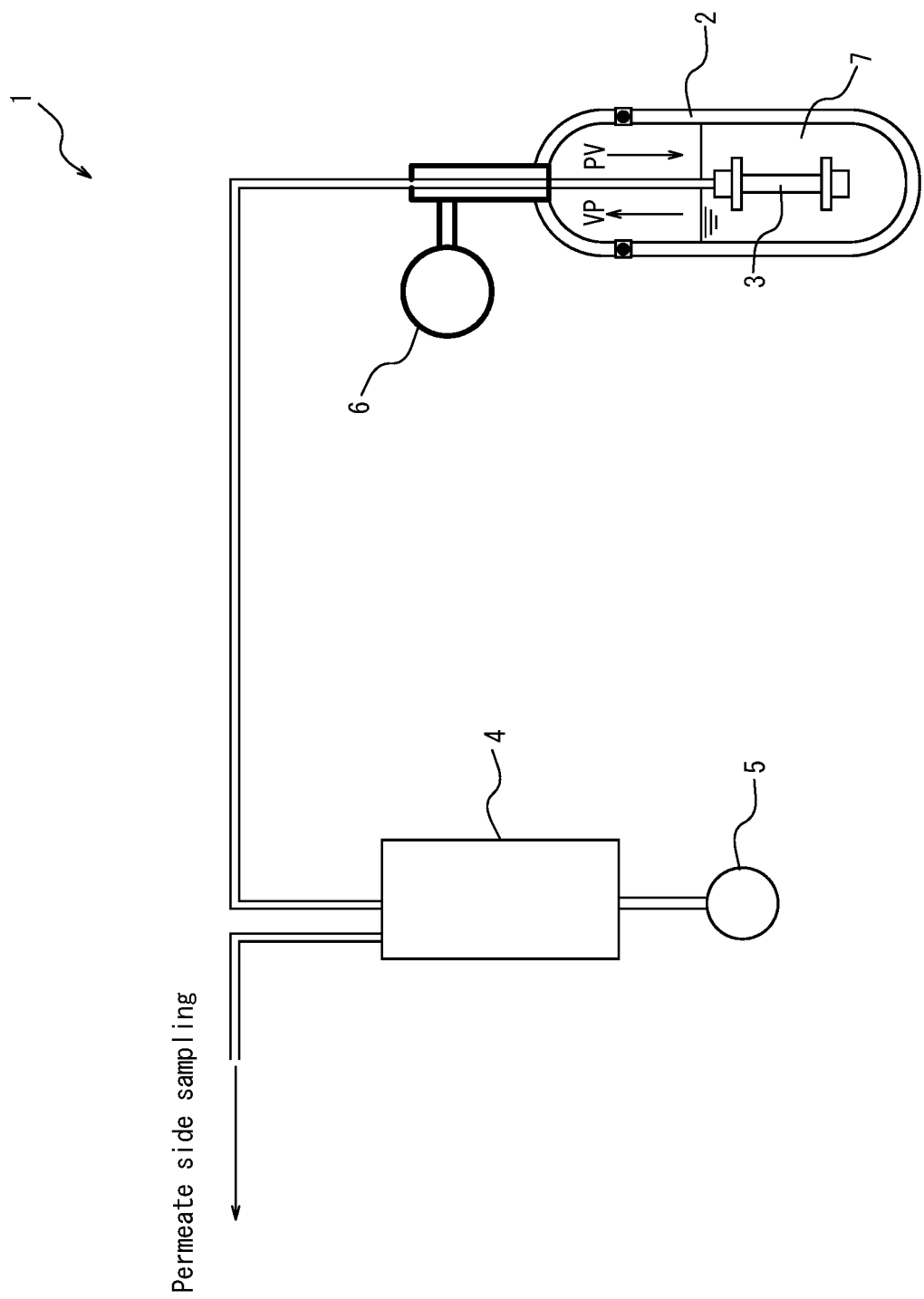

ZEOLITE MEMBRANE COMPOSITE, AND SEPARATION METHOD AND PRODUCTION METHOD OF BRANCHED DIOLEFIN USING SAME

TECHNICAL FIELD

The present disclosure relates to a zeolite membrane composite and to a separation method and a production method of a branched diolefin using this zeolite membrane composite, and, in particular, relates to a zeolite membrane composite that can suitably be used in separation of a branched diolefin from a branched hydrocarbon mixture, and to a separation method and a production method of a branched diolefin using this zeolite membrane composite.

BACKGROUND

Membrane separation is conventionally used as a low-energy method for separating a specific hydrocarbon from a hydrocarbon mixture containing a plurality of hydrocarbons differing in terms of the number of carbon-carbon unsaturated bonds included therein. Zeolite membranes that are obtained by forming a zeolite in a film-like form on a support are widely used as separation membranes.

For example, Patent Literature (PTL) 1 discloses a method of selectively separating an olefin from an olefin/paraffin mixed fluid using a zeolite membrane composite in which a membrane of an X-type zeolite is formed on a porous support. In PTL 1, a Ag—X-type zeolite in which cations of an X-type zeolite that are ion exchangeable have undergone ion exchange with Ag ions is used as the X-type zeolite.

CITATION LIST

Patent Literature

PTL 1: JP2015-174081A

SUMMARY

Technical Problem

The conventional Ag—X-type zeolite described above enables good separation of a paraffin from a monoolefin/paraffin mixed fluid (for example, an ethylene/ethane mixed fluid, an ethylene/propane mixed fluid, a propylene/ethane mixed fluid, or a propylene/propane mixed fluid) as an olefin/paraffin mixed fluid as has been verified in PTL 1. In recent years, there has been a need for a membrane separation technique that enables separation of a branched hydrocarbon including two carbon-carbon unsaturated bonds (i.e., a branched diolefin) from a branched hydrocarbon mixture containing a plurality of branched hydrocarbons that are of equivalent carbon number but differ in terms of the number of carbon-carbon unsaturated bonds included therein.

However, it has not been possible to selectively separate a branched diolefin from a branched hydrocarbon mixture containing a plurality of branched hydrocarbons that are of equivalent carbon number but differ in terms of the number of carbon-carbon unsaturated bonds included therein using the conventional Ag—X-type zeolite described above.

Accordingly, one object of the present disclosure is to provide a zeolite membrane composite that enables selective separation of a branched diolefin from a branched hydrocarbon mixture containing a plurality of branched hydrocarbons of equivalent carbon number that differ in terms of the number of carbon-carbon unsaturated bonds included therein.

Another object of the present disclosure is to provide a method of separating a branched diolefin that enables selective separation of a branched diolefin from a branched hydrocarbon mixture containing a plurality of branched hydrocarbons of equivalent carbon number that differ in terms of the number of carbon-carbon unsaturated bonds included therein.

Yet another object of the present disclosure is to provide a method of producing a branched diolefin that includes selectively separating a branched diolefin in accordance with a presently disclosed separation method.

Solution to Problem

The inventor conducted diligent studies to achieve these objects. As a result, the inventor reached a new finding that through a zeolite membrane composite obtained through film formation on a porous support of an X-MOR-type zeolite that is obtained by causing ionic bonding of a specific metal ion X at a cation site of a MOR-type zeolite, it is possible to selectively separate a branched diolefin from a branched hydrocarbon mixture containing a plurality of branched hydrocarbons of equivalent carbon number that differ in terms of the number of carbon-carbon unsaturated bonds included therein. The inventor completed the present disclosure based on the new finding set forth above.

Specifically, the present disclosure aims to advantageously solve the problem set forth above, and a presently disclosed zeolite membrane composite comprises: a porous support; and a zeolite membrane formed on at least one surface of the porous support, wherein the zeolite membrane is formed of an X-MOR-type zeolite, and X includes at least one type of transition metal ion.

Through a zeolite membrane composite including a zeolite membrane formed of a MOR-type zeolite that has at least one type of transition metal ion ionically bonded at a cation site in this manner, it is possible to selectively separate a branched diolefin from a branched hydrocarbon mixture containing a plurality of branched hydrocarbons of equivalent carbon number that differ in terms of the number of carbon-carbon unsaturated bonds included therein.

In the presently disclosed zeolite membrane composite, the transition metal ion preferably includes at least one among a Ru ion, a Pt ion, and a Mo ion. Through a zeolite membrane composite including a zeolite membrane formed of a MOR-type zeolite having at least one among a Ru ion, a Pt ion, and a Mo ion ionically bonded at a cation site in this manner, a branched diolefin can be even more selectively separated.

In the presently disclosed zeolite membrane composite, the transition metal ion is preferably a Ru ion. Through a zeolite membrane composite including a zeolite membrane formed of a MOR-type zeolite having a Ru ion ionically bonded at a cation site, a branched diolefin can be even more selectively separated.

In the presently disclosed zeolite membrane composite, the Ru ion is preferably a trivalent Ru ion. When a Ru ion that is ionically bonded at a cation site in the MOR-type zeolite of the presently disclosed zeolite membrane composite is a trivalent Ru ion, a branched diolefin can be even more selectively separated. In addition, a zeolite membrane composite having a trivalent Ru ion as a Ru ion that is ionically bonded at a cation site has excellent ease of production.

Moreover, the present disclosure aims to advantageously solve the problem set forth above, and a presently disclosed method of separating a branched diolefin comprises a separation step of using any one of the zeolite membrane composites set forth above to separate a branched diolefin from a branched hydrocarbon mixture containing the branched diolefin and at least one branched hydrocarbon in which the number of carbon-carbon double bonds is 1 or less and that is of an equivalent carbon number n to the branched diolefin. By using the presently disclosed zeolite membrane composite set forth above to perform separation of a branched hydrocarbon mixture containing a plurality of branched hydrocarbons of equivalent carbon number that differ in terms of the number of carbon-carbon unsaturated bonds included therein, it is possible to selectively separate a branched diolefin.

In the presently disclosed method of separating a branched diolefin, the carbon number n is preferably 4 or 5. Through the presently disclosed method of separating a branched diolefin, it is possible to selectively separate a branched diolefin from a branched hydrocarbon mixture containing a plurality of branched hydrocarbons of an equivalent carbon number of 4 or 5 that differ in terms of the number of carbon-carbon unsaturated bonds included therein.

Furthermore, the present disclosure aims to advantageously solve the problem set forth above, and a presently disclosed method of producing a branched diolefin comprises separating the branched diolefin in accordance with any one of the methods of separating a branched diolefin set forth above.

Advantageous Effect

According to the present disclosure, it is possible to provide a zeolite membrane composite that enables selective separation of a branched diolefin from a branched hydrocarbon mixture containing a plurality of branched hydrocarbons of equivalent carbon number that differ in terms of the number of carbon-carbon unsaturated bonds included therein.

Moreover, according to the present disclosure, it is possible to provide a method of separating a branched diolefin that enables selective separation of a branched diolefin from a branched hydrocarbon mixture containing a plurality of branched hydrocarbons of equivalent carbon number that differ in terms of the number of carbon-carbon unsaturated bonds included therein.

Furthermore, according to the present disclosure, it is possible to produce a branched diolefin through selective separation of the branched diolefin in accordance with the presently disclosed method of separating a branched diolefin.

BRIEF DESCRIPTION OF THE DRAWING

In the accompanying drawing,
FIG. 1 illustrates the schematic configuration of a test apparatus used in examples and a comparative example.

DETAILED DESCRIPTION

The following provides a detailed description of embodiments of the present disclosure.

The presently disclosed zeolite membrane composite is used in separation of a branched diolefin from a branched hydrocarbon mixture containing a plurality of branched hydrocarbons of equivalent carbon number that differ in terms of the number of carbon-carbon unsaturated bonds included therein.

(Zeolite Membrane Composite)

The presently disclosed zeolite membrane composite is a zeolite membrane composite that includes a porous support and a zeolite membrane formed on at least one surface of the porous support. In particular, the zeolite membrane is formed of an X-MOR-type zeolite. When a zeolite membrane is said to be "formed of an X-MOR-type zeolite" in the present specification, this means that the zeolite membrane contains an X-MOR-type zeolite, preferably that more than 50 mass % of zeolite forming the zeolite membrane is an X-MOR-type zeolite, and more preferably that all zeolite forming the zeolite membrane is an X-MOR-type zeolite. Moreover, "X" includes at least one type of transition metal ion. The term "X-MOR-type zeolite" refers to a MOR-type zeolite in which a metal ion X is ionically bonded at a cation site of the MOR-type zeolite.

As a result of the presently disclosed zeolite membrane composite including a zeolite membrane formed of a MOR-type zeolite having at least one type of transition metal ion ionically bonded at a cation site, the presently disclosed zeolite membrane composite enables selective separation of a branched diolefin from a branched hydrocarbon mixture containing a plurality of branched hydrocarbons of equivalent carbon number that differ in terms of the number of carbon-carbon unsaturated bonds included therein.

Zeolite membranes formed of various types of zeolites have conventionally been subjected to ion exchange to cause bonding of ions at cation sites of the zeolite, and thereby adjust the size of pores of the zeolite to a desired size. Attempts have been made to produce zeolite membranes having a desired pore size through various changes made to the combination of the type of zeolite and the ion used in ion exchange. Branched diolefins have a larger size than linear hydrocarbons that have been subjects of conventional membrane separation. Accordingly, it is necessary to adopt a zeolite membrane having a suitable pore size for a branched diolefin in order to allow the branched diolefin to pass therethrough. On the other hand, in a situation in which a zeolite is subjected to ion exchange to cause bonding of a certain ion at a cation site, the pore size decreases by a corresponding amount.

As a result of diligent studies, the inventor succeeded in selectively separating a branched diolefin from a branched hydrocarbon mixture containing a plurality of branched hydrocarbons of equivalent carbon number that differ in terms of the number of carbon-carbon unsaturated bonds included therein by adopting a MOR-type zeolite from among various types of zeolites and by adopting at least one type of transition metal ion as a metal ion used in ion exchange. Although the reason for this is not clear, it is presumed to be as follows. A transition metal ion ionically bonded to a MOR-type zeolite is thought to have high affinity with a branched diolefin according to interpretation based on HSAB (Hard and Soft Acids and Bases) theory. Consequently, when an X-MOR-type zeolite in which such ions are ionically bonded and a specific hydrocarbon mixture containing a branched diolefin are brought into contact, the branched diolefin can coordinate bond with suitable strength to a transition metal ion that is ionically bonded to the X-MOR-type zeolite. A branched diolefin molecule that has temporarily become coordinate bonded can easily be replaced by another branched diolefin molecule that is subsequently supplied. The branched diolefin that is released from coordinate bonding can then move to the permeate side by passing through a pore of the zeolite membrane. The successive occurrence of this phenomenon is thought to result in a branched diolefin selectively passing through the zeolite membrane formed of the X-MOR-type zeolite. Among transition metal ions, this trend is thought to be particularly noticeable for Ru ions, Pt ions, and Mo ions. Accordingly, it is preferable that the transition metal ion serving as X includes at least one among a Ru ion, a Pt ion, and a Mo ion from a viewpoint of increasing selective permeability of a branched diolefin.

<Porous Support>

In the presently disclosed zeolite membrane composite, the porous support that supports a zeolite membrane on at least one surface thereof is a porous body that includes a plurality of pores. The porous support may have any shape such as a flat film shape, a flat plate shape, a tube shape, or a honeycomb shape without any specific limitations. The material of the porous support is not specifically limited and may be a support that is a porous body formed of a porous ceramic such as alumina, mullite, zirconia, cordierite, or silicon carbide; a glass such as shirasu porous glass; or a porous sintered metal such as stainless steel. The average pore diameter of the porous support can be not less than 100 nm and not more than 5 μm, for example.

<Zeolite Membrane>

The zeolite membrane is a membrane obtained through film formation of an X-MOR-type zeolite. The MOR-type zeolite is a zeolite having a mordenite (MOR) crystal structure. A MOR-type crystal structure is defined in a database provided by the International Zeolite Association.

The thickness of the zeolite membrane can be not less than 1 μm and not more than 50 μm, for example. A zeolite membrane composite in which the thickness of the zeolite membrane is within the range set forth above enables even more selective separation of a branched diolefin.

The "thickness of the zeolite membrane" can be measured using a scanning electron microscope (SEM). The thickness of the zeolite membrane can be controlled by, for example, adjusting the average particle diameter of seed crystals used to form the zeolite membrane, the synthesis conditions of the zeolite (temperature, time, etc.), and so forth.

<Metal Ion X>

The metal ion X is present in an ionically bonded state at a cation site of the MOR-type zeolite. The metal ion X includes at least one type of transition metal ion.

Among transition metal ions, Ag ions, Cu, ions, and Au ions that have generally been used for ion exchange of zeolite membranes in zeolite membrane composites conventionally used for separating hydrocarbons, as well as various alkali metal ions, etc., have the potential to form explosive acetylides in a case in which a separation subject contains acetylene. For example, acetylene may be contained in a case in which a hydrocarbon mixture obtained through various purification operations in a purification process of petroleum is used as a separation subject. For this reason, it has conventionally been difficult to adopt a separation method using a zeolite membrane composite in a purification operation performed at a specific stage in a purification process of petroleum. However, acetylides are not formed when the transition metal ion serving as the metal ion X is a Ru ion, a Pt ion, or a Mo ion. Therefore, in a case in which at least one of a Ru ion, a Pt ion, and a Mo ion is used as the metal ion X in the presently disclosed zeolite membrane composite, it is possible to adopt a separation operation by membrane separation even in a purification operation performed at a specific stage in a purification process of petroleum, where it has not conventionally been possible to adopt a separation method by membrane separation.

Of transition metal ions, it is preferable that the transition metal ion serving as the metal ion X includes a Ru ion, and more preferable that the transition metal ion serving as the metal ion X includes a trivalent Ru ion. Through a zeolite membrane composite including a zeolite membrane formed of a MOR-type zeolite having a Ru ion, and particularly a trivalent Ru ion, ionically bonded at a cation site, a branched diolefin can be even more selectively separated. Although a divalent Ru ion can theoretically be envisaged as the Ru ion, a compound that can be used to cause ionic bonding of a trivalent Ru ion at a cation site is easier to acquire than a compound that can be used to cause ionic bonding of a divalent Ru ion at a cation site. Consequently, a zeolite membrane composite that contains a trivalent Ru ion as the metal ion X has excellent ease of production.

<Production Method of Zeolite Membrane Composite>

The presently disclosed zeolite membrane composite including a zeolite membrane having the properties set forth above can be produced through a seed crystal adhesion step of adhering zeolite seed crystals to the porous support to obtain a seed crystal-bearing support, a zeolite membrane formation step of forming a zeolite membrane formed of a zeolite on the seed crystal-bearing support, and an ion exchange step of performing ion exchange treatment of the zeolite membrane.

Operations in each of these steps can be performed in accordance with a known zeolite membrane formation method without any specific limitations.

<Seed Crystal Adhesion Step>

In the seed crystal adhesion step, zeolite seed crystals may be adhered to (mounted on) the porous support by a known technique such as coating or rubbing. More specifically, MOR-type zeolite seed crystals may be adhered to the porous support in the seed crystal adhesion step by applying, onto the porous support, a dispersion liquid obtained by dispersing MOR-type zeolite seed crystals in water, and then drying the dispersion liquid that has been applied.

Note that the MOR-type zeolite seed crystals may be a commercially available MOR-type zeolite or may be produced in accordance with a known method. Also note that the MOR-type zeolite may be subjected to micronization or the like as necessary.

<Zeolite Membrane Formation Step>

In the zeolite membrane formation step, the porous support to which the MOR-type zeolite seed crystals have been adhered is immersed in an aqueous sol containing a silica source, a mineralizer, an aluminum source, and so forth, and a zeolite membrane containing a MOR-type zeolite is synthesized by hydrothermal synthesis. The porous support including the zeolite membrane obtained in the zeolite membrane formation step may optionally be subjected to a boil washing operation and/or a firing operation.

The silica source may be colloidal silica, wet silica, amorphous silica, fumed silica, sodium silicate, silica sol, silica gel, kaolinite, diatomite, white carbon black, tetrabutoxysilane, tetrabutyl orthosilicate, tetraethoxysilane, or the like, for example, without any specific limitations. Of these silica sources, colloidal silica can suitably be used.

The mineralizer may be NaOH or the like, for example, without any specific limitations.

The aluminum source may be $NaAlO_2$ or $Al(OH)_3$, for example, without any specific limitations. Of these aluminum sources, $NaAlO_2$ can suitably be used.

Although no specific limitations are placed on the mixing ratio of various compounding agents in production of the aqueous sol used in the zeolite membrane formation step, the mixing ratio of silica source:aluminum source, as a molar ratio, is preferably 1:0.003 to 1:0.1.

<<Immersion>>

The method by which the porous support having MOR-type zeolite seed crystals adhered thereto is immersed in the aqueous sol is not specifically limited and may, for example, be a method in which the aqueous sol is loaded into a pressure-resistant vessel housing the porous support having MOR-type zeolite seed crystals adhered thereto. Alternatively, a method in which the porous support having MOR-type zeolite seed crystals adhered thereto is loaded into a pressure-resistant vessel housing the aqueous sol may be adopted.

<<Hydrothermal Synthesis>>

The heating temperature during heating of the aqueous sol in which the porous support having MOR-type zeolite seed crystals adhered thereto is immersed and synthesis of a MOR-type zeolite by hydrothermal synthesis to form a zeolite membrane on the porous support is preferably not lower than 100° C. and not higher than 250° C., and more preferably not lower than 150° C. and not higher than 200° C. The heating time is preferably not less than 1 hour and not more than 50 hours, and more preferably not less than 2 hours and not more than 20 hours. Examples of methods by which the aqueous sol and the porous support in the pressure-resistant vessel can be heated include a method in which the pressure-resistant vessel is heated in a hot-air dryer and a method in which the pressure-resistant vessel is heated by a directly attached heater. Once hydrothermal synthesis has ended, the porous support including the obtained zeolite membrane may be subjected to brushing. This brushing can remove amorphous material adhered to the zeolite membrane obtained as a result of hydrothermal synthesis. The selectivity of separation by the zeolite membrane can be further increased by performing brushing.

<<Boil Washing Operation>>

In a situation in which the porous support including the zeolite membrane obtained as described above is subjected to boil washing, the washing liquid may be distilled water, for example. The boil washing time is preferably not less than 10 minutes and not more than 2 hours, and more preferably not less than 30 minutes and not more than 1.5 hours. Note that the boil washing may be repeated (for example, 2 or 3 times) and that the repetitions of the boil washing may each be carried out under the same boil washing conditions or different boil washing conditions. Drying treatment may be performed after the boil washing as necessary. The drying temperature of the porous support including the zeolite membrane after boil washing is preferably 70° C. or higher, and is preferably 200° C. or lower, and more preferably 180° C. or lower. Moreover, the drying time can be not less than 1 hour and not more than 48 hours, for example.

<Ion Exchange Step>

In the ion exchange step, the zeolite membrane that has been formed on the porous support is subjected to ion exchange treatment to cause ionic bonding of a desired metal ion X at a cation site. The ion exchange treatment can be performed by, for example, immersing the zeolite membrane in a solution containing the desired metal ion X. Moreover, a washing operation and a vacuum drying operation can optionally be performed after the immersion.

The solution containing the metal ion X may be a solution that is obtained by dissolving a compound that includes the metal ion X in distilled water, ultrapure water, or the like. The compound including the metal ion X that is used in production of the solution may be $RuCl_3$, $Ru(NH_3)_6Cl_3$, or the like, for example, without any specific limitations. The temperature during immersion of the zeolite membrane in the solution containing the metal ion X is not specifically limited and can be not lower than 10° C. and not higher than 100° C., for example.

(Method of Separating Branched Diolefin)

The presently disclosed method of separating a branched diolefin involves performing a separation step of using the presently disclosed zeolite membrane composite set forth above to separate a branched diolefin from a branched hydrocarbon mixture containing the branched diolefin and at least one branched hydrocarbon in which the number of carbon-carbon double bonds is 1 or less and that is of an equivalent carbon number n to the branched diolefin. In the presently disclosed method of separating a branched diolefin, the branched diolefin can be selectively separated as a result of separation of the branched hydrocarbon mixture being performed using the presently disclosed zeolite membrane composite. The carbon number n of the branched hydrocarbon mixture that is a separation subject in the presently disclosed method of separating a branched diolefin is preferably 4 or 5.

<Branched Hydrocarbon Mixture>

The branched hydrocarbon mixture can contain branched diolefins, branched monoolefins, and branched alkanes of an equivalent carbon number n to one another, and can also contain other hydrocarbons. Note that the carbon number n is an integer, is preferably 4 or 5, and is more preferably 5. In more detail, the branched hydrocarbon mixture contains a branched diolefin of the carbon number n and either or both of a branched monoolefin of the carbon number n and a branched alkane of the carbon number n as main components, and may further contain a hydrocarbon of any carbon number. Note that when the branched hydrocarbon mixture is said to "contain a branched diolefin of the carbon number n and either or both of a branched monoolefin of the carbon number n and a branched alkane of the carbon number n as main components", this means that the branched hydrocarbon mixture contains 50 mass % or more, in total, of a branched diolefin of the carbon number n and either or both of a branched monoolefin of the carbon number n and a branched alkane of the carbon number n. For example, in a case in which the carbon number n of the branched hydrocarbon mixture is 5, the branched hydrocarbon mixture may contain isoprene (number of carbon-carbon double bonds: 2) and may also contain either or both of isopentane (number of carbon-carbon double bonds: 0) and a compound in which the number of carbon-carbon double bonds is 1, such as 2-methyl-1-butene, 2-methyl-2-butene, or 3-methyl-1-butene, and the total proportion constituted thereby in the overall branched hydrocarbon mixture may be 50 mass % or more.

<Separation Step>

In the separation step of the presently disclosed method of separating a branched diolefin, a branched diolefin is separated from a branched hydrocarbon mixture such as described above. The separation step can be implemented by vapor permeation (VP), pervaporation (PV), or the like without any specific limitations. The separation step is preferably carried out under heated conditions. Specifically, the separation step can be carried out under conditions of preferably not lower than 20° C. and not higher than 300° C., more preferably not lower than 25° C. and not higher than 250° C., and even more preferably not lower than 50° C. and not higher than 200° C.

The separation step may be performed repeatedly. In other words, separated material obtained through an $m^{th}$ separation step may be subjected to an $(m+1)^{th}$ separation step. By using obtained separated material as a separation subject for a further separation step, it is possible for a higher overall separation selectivity to be displayed than the separation selectivity that can be obtained when the separation step is performed just once. The number of repetitions of the separation step that are implemented can be freely set, for example, in accordance with a separation factor $\alpha$, which can be calculated by a method described in the EXAMPLES section of the present specification.

(Method of Producing Branched Diolefin)

The presently disclosed method of producing a branched diolefin includes separating a branched diolefin from a specific branched hydrocarbon mixture in accordance with the presently disclosed method of separating a branched diolefin set forth above. In the presently disclosed method of producing a branched diolefin, a branched diolefin can be separated by membrane separation, and thus the branched diolefin can be produced with low-energy (i.e., can be produced efficiently) compared to a conventional method. The specific branched hydrocarbon mixture is a mixture containing a branched diolefin and at least one branched hydrocarbon in which the number of carbon-carbon double bonds is 1 or less and that is of an equivalent carbon number n to the branched diolefin as previously described. Details pertaining to this mixture are as previously described in detail in the "Branched hydrocarbon mixture" section. Moreover, operations previously described in detail in the "Separation step" section can suitably be performed in separation of the branched diolefin. The presently disclosed method of producing a branched diolefin may include a purification step of purifying the obtained branched diolefin, implemented at a later stage than the separation step. Examples of purification steps that can be implemented include, but are not specifically limited to, steps that are performed by distillation and chromatographic separation.

EXAMPLES

The following provides a more specific description of the present disclosure based on examples. However, the present disclosure is not limited to the following examples. In the following description, "%" and the like used to express quantities are by mass, unless otherwise specified.

In the examples and comparative example, analysis of an obtained zeolite membrane composite was performed by methods described below, and separation performance of the zeolite membrane composite was calculated by a method described below.

<Analysis of Zeolite Membrane Composite>
<<X-Ray Diffraction Pattern>>

An X-ray diffractometer (Discover D8 produced by Bruker AXS) was used to obtain an X-ray diffraction pattern of a porous separation layer. The measurement conditions were as follows.

X-ray source: Cu-Kα radiation
Wavelength λ: 1.54 Angstroms
Tube voltage: 30 kV
Tube current: 15 mA
Power: 0.9 kW
Incident slit: Length 1.0 mm×width 1.0 mm
Receiving slit: Soller slit (angular resolution 0.35 deg)
Detector: Scintillation counter
Measurement rate: 0.01 deg/s
<<SEM-EDX Analysis>>

Ions ionically bonded at cation sites in a zeolite membrane of a zeolite membrane composite obtained in each example or comparative example were analyzed by SEM-EDX (Scanning Electron Microscope-Energy Dispersive X-ray Spectroscopy). The analysis conditions were as follows.

SEM main body: S-3400N EDX produced by Hitachi High-Technologies Corporation
Detector: XFlash Detector 4010 produced by Bruker Corporation
Accelerating voltage: 15 kV
Current: 60 µA to 90 µA
Magnification: 3 k
ICR: 1.5 kcps
<Separation Performance of Zeolite Membrane Composite>

The results of a separation test were used to calculate the permeation flux F using the following equation (I). The separation factor $\alpha$ was calculated using the following equation (II). Note that a hydrocarbon mixture of isopentane (branched alkane having carbon number of 5) and isoprene (branched diolefin having carbon number of 5) was used as a separation subject.

$$F = W/(A \times t) \qquad (I)$$

$$\alpha = (Y_d/Y_a)/(X_d/X_a) \qquad (II)$$

In equation (I), W is the mass [kg] of permeate that has passed through the zeolite membrane composite, A is the effective area [m$^2$] of the zeolite membrane composite, and t is the processing time [h]. In equation (II), $Y_d$ is the proportional content [mass %] of isoprene in a permeate side sample, $Y_a$ is the proportional content [mass %] of isopentane in the permeate side sample, $X_d$ is the proportional content [mass %] of isoprene in the separation subject, and $X_a$ is the proportional content [mass %] of isopentane in the separation subject.

A larger value for the separation factor $\alpha$ indicates that the zeolite membrane composite has higher isoprene selectivity.

Example 1

<Seed Crystal Adhesion Step>

MOR-type zeolite seed crystals (NSZ-642NAA produced by Tosoh Corporation) were applied onto a tube-shaped porous α-alumina support (external diameter: 2.5 mm; average pore diameter: 150 nm) serving as a porous support by a coating method and were dried to obtain a porous support having MOR-type zeolite seed crystals adhered thereto (hereinafter, referred to as a "seed crystal-bearing support").

<Zeolite Membrane Formation Step>

Stirring of 2.16 g of NaOH as a mineralizer, 0.09 g of NaAlO$_2$ as an aluminum source, 20.13 g of colloidal silica as a silica source, and 34.77 g of ultrapure water was performed at 50° C. for 4 hours to yield an aqueous sol for zeolite membrane formation. The composition of this aqueous sol, as a molar ratio, was SiO$_2$:Na$_2$O:Al$_2$O$_3$:H$_2$O=36:10:0.2:960.

The aqueous sol obtained as described above was loaded into a pressure-resistant synthesis vessel. Next, the seed crystal-bearing support obtained in the seed crystal adhesion step was immersed in the aqueous sol inside the pressure-resistant synthesis vessel, and a reaction (hydrothermal synthesis) was carried out at 165° C. for 6 hours to form a zeolite membrane on the porous support. The porous support including the obtained zeolite membrane was subjected to brushing and was subsequently subjected to 60 minutes of boil washing in boiled distilled water. Thereafter, the porous support including the zeolite membrane was dried for 12 hours in an 85° C. thermostatic dryer.

<Ion Exchange Step>

The porous support including the zeolite membrane obtained in the step described above was immersed in $RuCl_3$ aqueous solution of 0.005 M in concentration and was held therein at 50° C. for 3 hours to perform ion exchange. The obtained porous support including the zeolite membrane that had undergone ion exchange was water washed and was then dried at 85° C. for 12 hours to obtain a zeolite membrane composite.

The zeolite membrane of the zeolite membrane composite obtained through the step described above was measured by X-ray diffraction to obtain an X-ray diffraction pattern. The zeolite membrane was confirmed to have a MOR-type structure based on the obtained X-ray diffraction pattern. It was also confirmed as a result of SEM-EDX analysis that Ru ions were ionically bonded at cation sites in the obtained MOR-type zeolite membrane.

<Separation Test>

The zeolite membrane composite obtained as described above was used to perform a separation test using a test apparatus 1 such as illustrated in FIG. 1.

<<Test Apparatus>>

The test apparatus 1 illustrated in FIG. 1 includes a feedstock tank 2, a zeolite membrane composite 3, and a cold trap 4. The test apparatus 1 also includes a vacuum pump 5 downstream of the cold trap 4. The internal pressure of the feedstock tank 2 is controlled to a pressure indicated by a pressure gauge 6 through adjustment of the external temperature. Moreover, the zeolite membrane composite 3 inside the feedstock tank 2 is moved by a control mechanism (not illustrated) such as to be in contact with a liquid phase or gas phase hydrocarbon mixture 7. The zeolite membrane composite 3 illustrated in FIG. 1 is a tubular body, and a permeate that selectively passes through the zeolite membrane penetrates to the inside of the tube.

In the test apparatus 1, the permeate side of the zeolite membrane composite 3 is placed in a reduced pressure state by the vacuum pump 5 such that a permeate that has passed through the zeolite membrane composite 3 is fed to the cold trap 4. Permeate that has been restored to a liquid phase through cooling by the cold trap 4 can be extracted as a permeate side sample.

<<Membrane Separation>>

The separation test was implemented as follows using the test apparatus 1 illustrated in FIG. 1.

Specifically, a hydrocarbon mixture containing 50 mass % each of isoprene and isopentane was first loaded into the feedstock tank 2 and was then heated to 70° C. by a heating mechanism (not illustrated). The zeolite membrane composite 3 was then moved by the control mechanism (not illustrated) such that the liquid phase hydrocarbon mixture was in contact with the zeolite membrane composite 3. The vacuum pump 5 located downstream of the cold trap 4 was used to place the permeate side in a reduced pressure state (3 kPaA). In other words, in Example 1, separation performance was evaluated for a case in which the separation step was performed by pervaporation (PV). Permeate (gas phase) that had passed through the zeolite membrane composite 3 was restored to a liquid phase through cooling by the cold trap 4, and permeate that passed for 30 minutes from the start of separation was sampled. The mass of the permeate side sample that had been taken was measured. Moreover, the concentrations (mass %) of isoprene and isopentane in the permeate side sample were measured using a gas chromatograph. These measured values were used to determine values for the separation factor $\alpha$ and the permeation flux F. The results are shown in Table 1.

Example 2

Separation performance was evaluated for a case in which the separation step was performed by vapor permeation (VP). With regards to the specific operations, the zeolite membrane composite 3 was moved by the control mechanism (not illustrated) such that a gas phase hydrocarbon mixture was in contact with the zeolite membrane composite 3 in the operations described in the "Membrane separation" section. With the exception of this point, a separation test was performed, and values for the separation factor $\alpha$ and the permeation flux F were determined in the same way as in Example 1. The results are shown in Table 1.

Comparative Example 1

A zeolite membrane composite was obtained in the same way as in Example 1 with the exception that the ion exchange step was not performed, and the obtained zeolite membrane composite was used to perform a separation test in the same way as in Example 1. In other words, in Comparative Example 1, a separation test was performed by PV using a zeolite membrane composite in which Na ions were ionically bonded and trivalent Ru ions were not ionically bonded at cation sites in a MOR-type zeolite membrane. Obtained values for the separation factor $\alpha$ and the permeation flux F are shown in Table 1. Moreover, the obtained zeolite membrane composite was confirmed to be a Na-MOR-type upon being analyzed as previously described.

TABLE 1

| | | | Example 1 | Example 2 | Comparative Example 1 |
|---|---|---|---|---|---|
| Separation subject | Carbon number n [carbons] | | 5 | 5 | 5 |
| | Type of branched diolefin | | Isoprene | Isoprene | Isoprene |
| | Type of branched alkane | | Isopentane | Isopentane | Isopentane |
| Zeolite membrane composite | Porous support | Pore diameter [nm] | 150 | 150 | 150 |
| | | Material | α Alumina | α Alumina | α Alumina |
| | Zeolite membrane | Type of zeolite | MOR | MOR | MOR |
| | Metal ion X | Type | Ru ion | Ru ion | Na ion |
| | | Valence | 3 | 3 | 1 |

TABLE 1-continued

|  |  | Example 1 | Example 2 | Comparative Example 1 |
|---|---|---|---|---|
| Separation step |  | PV | VP | PV |
| Separation performance | Permeation flux F [kg/m$^2$/h] | 0.0487 | 0.0545 | 0.0631 |
|  | Separation factor α [—] | 1.72 | 1.61 | 0.971 |
|  | F × α [—] | 0.0838 | 0.0877 | 0.0613 |

It can be seen from Table 1 that the value of the separation factor α was large and isoprene (branched diolefin) could be selectively separated from the branched hydrocarbon mixture containing isoprene and isopentane when the zeolite membrane composites of Examples 1 and 2, which each included a zeolite membrane formed of a Ru-MOR-type zeolite, were used. In contrast, it can be seen that the value of the separation factor α was smaller than in the examples and isoprene could not be selectively separated when the zeolite membrane composite of Comparative Example 1, which included a zeolite membrane formed of a MOR-type zeolite that had not undergone ion exchange (Na-MOR-type zeolite), was used.

It should be noted that although the permeation flux F was higher in Comparative Example 1 than in Examples 1 and 2, the value of an indicator (F×α) obtained by multiplying the separation factor α by the permeation flux F was larger in Examples 1 and 2 than in Comparative Example 1, and thus Examples 1 and 2 were superior to Comparative Example 1 in relation to performance of efficiently separating a desired branched diolefin.

INDUSTRIAL APPLICABILITY

According to the present disclosure, it is possible to provide a zeolite membrane composite that enables selective separation of a branched diolefin from a branched hydrocarbon mixture containing a plurality of branched hydrocarbons of equivalent carbon number that differ in terms of the number of carbon-carbon unsaturated bonds included therein.

Moreover, according to the present disclosure, it is possible to provide a method of separating a branched diolefin that enables selective separation of a branched diolefin from a branched hydrocarbon mixture containing a plurality of branched hydrocarbons of equivalent carbon number that differ in terms of the number of carbon-carbon unsaturated bonds included therein.

Furthermore, it is possible to produce a branched diolefin through selective separation of the branched diolefin in accordance with the presently disclosed method of separating a branched diolefin.

REFERENCE SIGNS LIST 1 test apparatus
2 feedstock tank
3 zeolite membrane composite
4 cold trap
5 vacuum pump
6 pressure gauge
7 hydrocarbon mixture

The invention claimed is:

1. A zeolite membrane composite comprising: a porous support; and a zeolite membrane formed on at least one surface of the porous support, wherein
the zeolite membrane is formed of an X-MOR-type zeolite, and
X includes at least one among a Ru ion, a Pt ion, and a Mo ion.

2. The zeolite membrane composite according to claim 1, wherein the transition metal ion is a Ru ion.

3. The zeolite membrane composite according to claim 2, wherein the Ru ion is a trivalent Ru ion.

4. A method of separating a branched diolefin comprising a separation step of using the zeolite membrane composite according to claim 1 to separate a branched diolefin from a branched hydrocarbon mixture containing the branched diolefin and at least one branched hydrocarbon in which the number of carbon-carbon double bonds is 1 or less and that is of an equivalent carbon number n to the branched diolefin.

5. The method of separating a branched diolefin according to claim 4, wherein the carbon number n is 4 or 5.

6. A method of producing a branched diolefin comprising separating the branched diolefin in accordance with the method of separating a branched diolefin according to claim 4.

* * * * *